United States Patent [19]
Badat et al.

[11] Patent Number: 5,209,825
[45] Date of Patent: May 11, 1993

[54] PREPARATION OF PURIFIED CONCENTRATED BDO

[75] Inventors: Hashim M. Badat, Houston, Tex.; Peter G. Gelblum, Philadelphia, Pa.; Robert E. Trotter, Hockessin, Del.

[73] Assignee: E. I. Du Pont de Nemours and Company, Wilmington, Del.

[21] Appl. No.: 691,155

[22] Filed: Apr. 24, 1991

Related U.S. Application Data

[63] Continuation-in-part of Ser. No. 252,967, Oct. 4, 1988, abandoned.

[51] Int. Cl.⁵ .......................... B01D 3/10; B01D 3/14
[52] U.S. Cl. ...................................... 203/29; 203/77; 203/80; 568/868; 549/429
[58] Field of Search .......... 203/29, 14, 18, 50, 203/77, 80, DIG. 6; 549/429; 568/868

[56] References Cited

U.S. PATENT DOCUMENTS

| | | | |
|---|---|---|---|
| 3,891,511 | 6/1975 | Danneil et al. | 203/84 |
| 4,175,009 | 11/1979 | Copelin | 203/96 |
| 4,197,248 | 4/1980 | Copelin et al. | 204/14 |
| 4,332,645 | 6/1982 | Müller et al. | 203/14 |
| 4,348,262 | 9/1982 | Stock et al. | 203/37 |
| 4,383,895 | 5/1983 | Ernst et al. | 203/77 |
| 4,419,189 | 12/1983 | Caracciolo | 203/77 |

Primary Examiner—Virginia Manoharan

[57] ABSTRACT

A distillation process for the preparation of purified concentrated BDO.

High boiling impurities, including color formers, precursors of color formers and tar formers are removed from the BDO early in the process and under mild conditions.

17 Claims, 1 Drawing Sheet

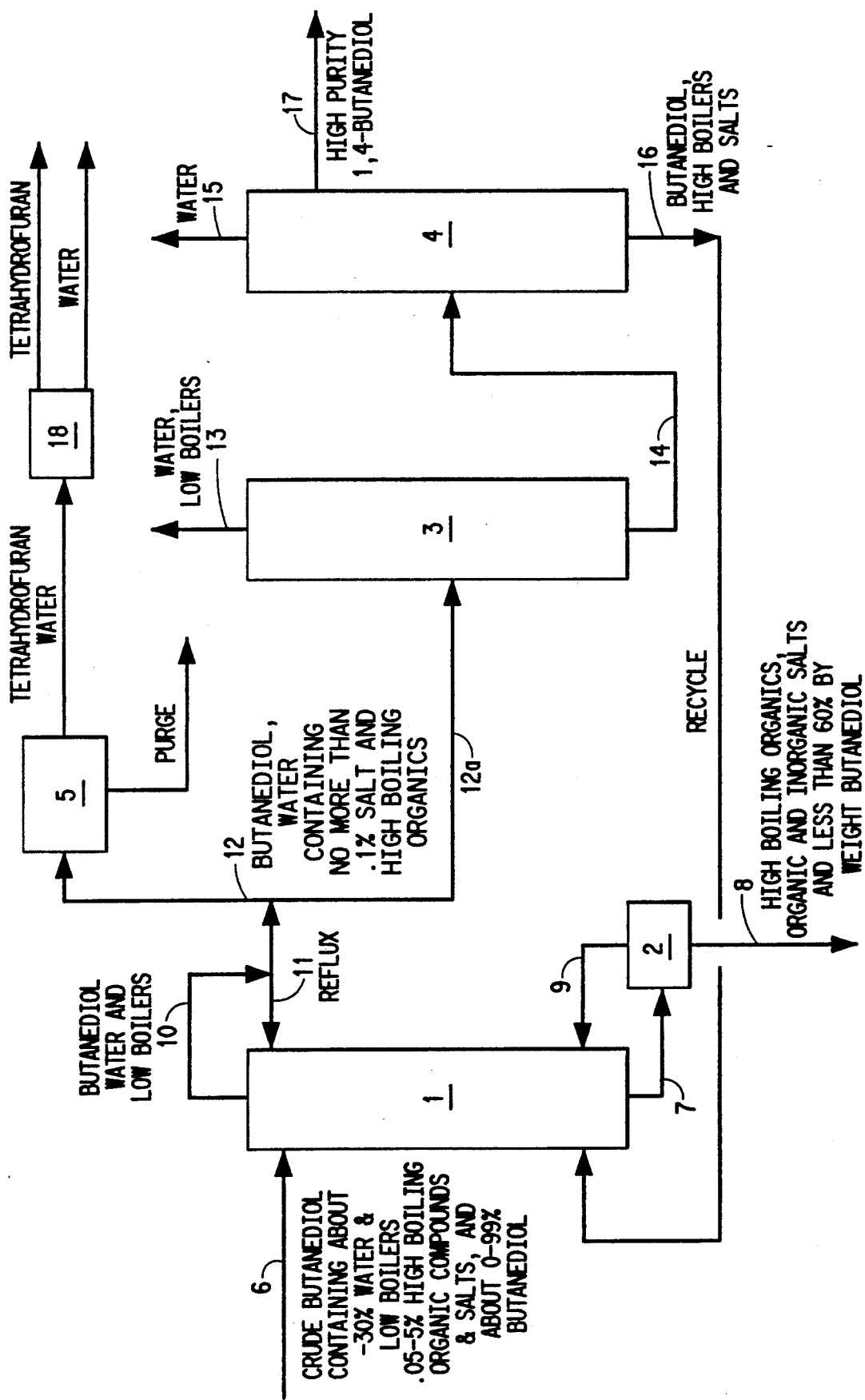

PREPARATION OF PURIFIED CONCENTRATED BDO

This application if a continuation-in-part of application Ser. No. 07/252,967 filed Oct. 4, 1988, now abandoned.

FIELD OF INVENTION

The process of the invention relates to a method of purification of crude 1,4-butanediol by removing color formers and precursors of color forming materials and precursors of tars by distillation. The color forming materials, precursors of color forming materials and precursors of tars are a portion of the high boiling organic compounds contained in the crude 1,4-butanediol. More specifically, the process of the invention relates to a process for removing color formers and precursors of the color formers and precursors of tar by first removing substantially all (99.9%) high boiling organic compounds, and organic salts and inorganic salts from crude 1,4-butanediol and subsequently removing water, low boiling impurities and remaining high boilers.

1,4-butanediol is sometimes hereinafter referred to as BDO.

BACKGROUND

The preparation of butynediol by the reaction of formaldehyde and acetylene, the subsequent hydrogenation of the butynediol to form crude 1,4-butanediol and the distillation of butanediol are described in U.S. Pat. No. 4,371,723.

Preparation of "very pure" 1,4-butanediol by fractional distillation of a water-free stream is described in U.S. Pat. No. 3,891,511.

When crude 1,4-butanediol is conventionally prepared from the starting materials, formaldehyde and acetylene using buffered reaction conditions, the resulting stream contains high boiling organic compounds, including color forming materials, precursors of color and tar formers, inorganic salts and organic salts including sodium formate that if not removed eventually from the BDO, give a product that is not suitable for high-volume, color sensitive end uses such as the formation of polyester, polyurethane and in the preparation of tetrahydrofuran. These high boiling compounds and salts, if not removed early in the purification process react with themselves and with BDO which produces tars and color formers; thus reducing the yield of BDO and reducing its utility. These wastes are economically undesirable, and are pollutants that pose difficult disposal problems.

Now it has been found that these impurities (high boilers including color forming materials and their precursors and precursors of tar, organic and inorganic salts) present in the crude BDO, can be removed very efficiently at very high yield by subjecting the crude BDO to distillation under mild conditions wherein the amount of these impurities is reduced to not more than 0.1% by weight based on the total organics. The purified concentrated BDO can be further distilled to remove water, low boilers and remaining high boilers to provide a BDO product for use in the color sensitive end uses, e.g., polyester, etc., or the purified concentrated BDO can be used to form a high purity colorless tetrahydrofuran. It has also been found that the yield from crude BDO to refined BDO and yield from crude BDO to tetrahydrofuran is greatly increased and that the purity of the finished product BDO and tetrahydrofuran is very high. An additional important feature of this invention resides in the fact that wastes can be minimized at the source.

SUMMARY OF THE INVENTION

The present invention is a process of refining crude BDO to a purified concentrated BDO.

Crude BDO contains 1–30% by weight water and organic impurities that boil lower than BDO, 0.05–5% by weight of high boiling organic compounds and inorganic and organic salts and 70 to 99% by weight BDO. Among the organic impurities are various undesirable color formers including those that are apparent when the BDO is mixed with acids such as hydrochloric acid, precursors of color formers and precursors of tar.

The process of this invention comprises, fractionation of the crude BDO feed stream at a temperature of no more than 210° C. and usually at a pressure in the range of about 40 to 80 torr, and separating as bottoms a fraction having a weight of not greater than 6% by weight of the feed stream, said bottoms containing high boiling organic compounds, inorganic and organic salts and not more than 60% by weight BDO.

Separating as lighter cut overhead a fraction containing substantially the same water content as in the crude BDO (about 1 to 30% by weight water) and no more than one-fifth the quantity of high boiling organic compounds and salts that were in the crude BDO, and based on total organics taken overhead not more than about 0.1% by weight high boiling organic compounds and salts. In other embodiments, the crude BDO and the purified concentrated 1,4-butanediol overhead fraction contained between about 1 and 15% by weight water, preferably between about 1 and 8% by weight water and most preferably between 4 and 6% by weight water.

The lighter cut overhead fraction may be further fractionated to remove components having a lower boiling point than BDO, such as water, low boiling alcohols and aldehydes, followed by the subsequent removal of the remaining quantities of 0.1% by weight high boilers and salts, or the high boilers may be removed first and then the low boilers removed from the lighter cut overhead fraction. The yield of purified refined 1,4-butanediol recovered at this point in the process will be at least 90% by weight, based on the weight of the crude butanediol used as a starting material in the process. Preferably, at this stage in the process, one will have formed a refined and purified 1,4-butanediol consisting essentially of 99.9% 1,4-butanediol and 0.05% high boiling compound. The latter may form color-forming compounds in the refined and purified 1,4-butanediol, but the APHA color of the polyester made from the refined and purified 1,4-butanediol will be no higher than 15. Moreover, in a preferred embodiment, the yield will be at least 95%.

Furthermore, all or a portion of the overhead stream may be directly used to make tetrahydrofuran by cyclization in an acidic reaction, yielding a high grade tetrahydrofuran at a high yield, e.g. about 94 to about 97% based on BDO in the overhead stream. The waste from this reaction is free flowing and clear. The free-flowing waste is soluble in water and in $C_1$ to $C_4$ alkanols.

The process of the present invention is particularly useful to purify a BDO stream made by the buffered reaction of formaldehyde and acetylene, followed by hydrogenation of the resulting butylenediol to form crude 1,4-butanediol. Such a crude stream contains a high boiling component, various organic and inorganic salts including alkali salts of formic acid, e.g. sodium formate, which if not removed early in the purification process react with other components in the mixture to form color-forming compounds.

BRIEF DESCRIPTION OF THE DRAWING

The figure is a flow sheet of the process of the present invention.

DETAILED DESCRIPTION

Referring now to the figure, a crude BDO feed stream 6, containing 1–30% by weight water and organic impurities that boil lower than BDO, 0.05–5% by weight of high boiling organic compounds and inorganic and organic salts and 70 to 99% by weight BDO is fed to distillation column 1, which is operated under mild conditions, for example, at pressure in the range of about 40 to 80 torr and at a temperature of no more than about 210° C., more preferably at 45 to 50 torr, and 175° to 185° C. Pressure of less than 40 torr may be employed —— temperature is a more significant factor than pressure in defining mild conditions.

The term "high boiling organic compounds" means compounds having a relative volatility of 0.7 and less where BDO has a volatility of 1.

From distillation column 1, stream 7 is separated and fed to the thin film evaporator 2, or similar low residence time, high mixing shear device for further fractionation. Stream 7, contains high boiling organic compounds, salts, and BDO.

From thin film evaporator 2, stream 8 is separated as residue. This stream contains not more than 6% by weight of stream 6 and contains high boiling organic compounds, salts and BDO. Stream 8 contains not more than 60% by weight BDO. Stream 8 has a honey-like consistency at room temperature and flows like water at 100° C.; moreover, it is soluble in $C_1$–$C_4$ alkanols and mixtures of water and one or more of said alkanols. Stream 9 from thin film evaporator 2 is returned to the distillation column 1 where it is again subjected to fractionation. Alternatively column 1 could be modified so as to include the functional features of a thin film evaporator, or just have more distillation plates, in which case, the stream 7 may be treated directly as residue without recovery of BDO.

The overhead stream 10 from column 1, which contains less than 0.1% by weight high boiling organic compounds, salts, mostly BDO, water and a small fraction of low boiling alcohols is split. A portion of the stream is sent back to column 1 as reflux 11 to aid in purifying the vapors coming up through column 1. The amount of stream that is refluxed will usually range from about 2% to 20% by weight of stream 10. All or a portion of the remaining portion of stream 10 may be used to form high purity tetrahydrofuran by sending it through stream 12 to reactor 5 where it is reacted under acid conditions at low pH and cyclized to form high purity tetrahydrofuran at high yield. The tetrahydrofuran may be separated from the water by azeotropic distillation apparatus 18. All or a portion of remaining stream 10 (labeled 12a) may be treated in subsequent distillation columns 3 and 4. The bottom stream leaving cyclizaton reactor 5 contains no more than 1% by weight of the feed purified concentrated 1,4-butanediol; that stream is free-flowing at below 100° C., and it is soluble in $C_1$ and $C_4$ alkanols and in mixtures of such alkanols with water.

In the figure, stream 12a is first fractionated to remove water and low boilers as overhead 13, resulting in a bottom stream 14 that contains BDO, and very small amount of high boiling organic compounds on the order of 0.1% by weight or less, based on total organics. The stream 14 is then subjected to further fractionation in column 4 where a further amount of this high boiling organic fraction is removed in bottom stream 16. Stream 16 is returned to the distillation column 1 where it is again subjected to fractionation. Stream 16 from the bottom of the distillation column 4 containing not more than 5% by weight of stream 14.

Very small overhead stream 15 is separated from the distillation column 4. Stream 15 is mostly water. Very high purity BDO is removed as a side draw stream 17 from the distillation column 4.

Alternatively stream 12a may be first subjected to distillation to further remove high boiling organic compounds and salts and then subjected to fractional distillation to remove water and low boilers.

EXAMPLE 1

In a three column embodiment of the process of invention crude BDO containing:

| BDO | = | 90.8% |
|---|---|---|
| Water | = | 6.07% |
| Low-boiling impurities | = | 0.4% |
| Close-boiling impurities | = | 0.6% |
| High-boiling impurities (including salts) | = | 2.13% |
| (Close-boiling impurities are compounds with relative volatility of about 0.8 to about 0.9, whereas High-boiling organic impurities are compounds with a relative volatility of 0.7 and less - where BDO has a volatility of 1.) | | | is fed at the mid point or lower of the first column. In the embodiment conventional packing or trays can be employed. In a preferred embodiment a mixture of trays and packing is used in the first column and packing is used in the second and third columns. In the embodiment it is sometimes desirable to have at least five theoretical trays below the feed point.

High boiling organic compounds and salts are removed from the bottom of the first column and fractionated in a low residence, high mixing shear device, e.g. thin film evaporator, removing 3% of the column feed stream containing concentrated high boiling organic compounds and salts comprising 40% BDO. The first column and thin film evaporator are operated at 45 torr pressure and 168° C. temperature and at 80 torr pressure and 185° C. temperature respectively.

The overhead product obtained from the first column has following composition:

| BDO | = | 92.63% |
|---|---|---|
| Water | = | 6.27% |
| Low-boiling Impurities | = | 0.41% |
| Close-boiling Impurities | = | 0.61% |
| High-boiling Impurities | = | 0.08% |

The overhead product from the first column is used in preparation of the colorless tetrahydrofuran and/or further distilled in the second and third column to obtain very high purity BDO free from color-forming impurities. The overhead product from the first column is fed to the second column at the mid point or lower but usually not below the packing i.e. at least five theoretical trays above the bottom. Low boilers and water are removed at the top, and bottom product containing high boilers and BDO is fed to the third column at the mid point. The second and third columns are operated at the pressure of 50 torr and bottom temperature of 165° C.

High boilers are removed in the bottom purge from the third column and recycled to the first column. A liquid stream, in a high yield of about 95 percent, contains BDO substantially free from high boiling organic compounds, salts, and color forming material is removed at point below the top packed section i.e. at least two theoretical trays below the top;

The product obtained as side draw has the following composition:

| | | |
|---|---|---|
| BDO yield | = | >95% |
| Color (APHA) | = | 0 |
| Polyester color | = | 15 |
| C O number | = | 0.013 |
| Purity | = | 99.911% |
| Water | = | 0.007% |
| Low-boiling impurities | = | 0.018% |
| Close-boiling impurities | = | 0.028% |
| High-boiling impurities | = | 0.036% |

The color formers and precursors of color formers and precursors of tar removed by the process of the invention are compounds that color the polyester products made from the reaction of BDO and dibasic acid. The color forming property is measured by first preparing a polyester with BDO and then following test procedure described as ASTM D-1209 to measure the color.

A portion of the BDO from the first column overhead is reacted in a continuous stirred reactor under acidic conditions at low pH and cyclized to form water and high purity tetrahydrofuran at at least 97% BDO to tetrahydrofuran yield.

The overhead product obtained from the reactor has following composition:

| | | |
|---|---|---|
| Water | = | 25% |
| Tetrahydrofuran | = | 75% |

A purge stream is separated from the bottom of the tetrahydrofuran reactor containing not more than 1% by weight of reactor feed containing unreacted BDO, organic tars, salts, high boilers and acid. The purge stream contains not more than 65% by weight BDO.

We claim:

1. A process of purifying crude 1,4-butanediol to purified concentrated 1,4-butanediol, said crude butanediol containing about 1 to about 30% by weight of water and organic impurities that boil lower than 1,4-butanediol, about 0.05 to about 5% by weight of high boiling organic compounds and inorganic and organic salts, and about 70 to 99% by weight of 1,4-butanediol, which consisting essentically of:

fractionating said crude butanediol feed stream at a temperature of no more than 210° C. into a purified concentrated 1,4-butanediol fraction and a bottom fraction;

separating as bottoms a fraction having a weight of not greater than 6% of the weight of said feed stream, said bottoms fraction containing high boiling organic compounds, inorganic and organic salts and not more than 60% by weight of 1,4-butanediol, and separating as overhead said purified concentrated 1,4-butanediol fraction which contains about the same amount of water as, and less high boiling organic compounds and inorganic and organic salts than, were in said crude butanediol feed stream, the amount of said high boiling organic compounds and said salts in said overhead fraction being not more than 0.1% by weight, based on the total organics.

2. The process of claim 1 in which overhead fraction is further fractionated to separate components having a boiling point lower than 1,4-butanediol.

3. The process of claim 2 in which the fraction remaining after separation of components having a lower boiling point than 1,4-butanediol is further fractionated so as to separate components having a higher boiling point than said butanediol, thereby forming a refined and purified 1,4-butanediol consisting essentially of 99.9% 1,4-butanediol and 0.05% high boiling compounds at a yield of at least 95% 1,4-butanediol, the APHA color of a polyester made from said refined and purified 1,4-butanediol being no greater than 15.

4. The process of claim 2 in which the fraction remaining after separation of components having a lower boiling point than 1,4-butanediol is further fractionated so as to separate components having a higher boiling point than said butanediol, thereby providing purified refined 1,4-butanediol in a yield of at least 90%.

5. The process of claim 4 wherein said yield is at least 95%.

6. The process of claim 4 wherein said bottoms fraction has a weight of not greater than 3% of the weight of said feed stream and contains no more than 40% by weight of 1,4-butanediol.

7. The process of claim 1 in which the overhead fraction is further fractionated to separate components having a higher boiling point than 1,4-butanediol.

8. The process of claim 1 in which one of salts in the crude 1,4-butanediol is sodium formate.

9. The process of claim 1 in which the crude BDO is obtained by the buffered reaction of formaldehyde and acetylene to form butynediol, following by hydrogenation of butynediol to form butanediol, and then concentrating that product.

10. The process of claim 1 in which the fractionation is carried out at a pressure in the range of about 40 to 80 torr.

11. The process of claim 1 wherein the water content in said crude butanediol and in said purified concentrated 1,4-butanediol fraction separated as overhead are both between about 1 and 15% by weight.

12. The process of claim 1 wherein the water content in said crude butanediol and in said purified concentrated 1,4-butanediol fraction separated as overhead are both between about 1 and 8% by weight.

13. The process of claim 1 wherein the water content in said crude butanediol and in said purified concentrated 1,4-butanediol fraction separated as overhead are both between about 4 and 6% by weight.

14. The process of claim 1 wherein a portion of said overhead fraction is cyclized and distilled to form high purity non-color-forming tetrahydrofuran in a yield of at least 94% based on said crude 1,4-butanediol.

15. The process of claim 14 in which the yield of tetrahydrofuran is at least about 97% based on the 1,4-butanediol fed to the cyclization reaction.

16. The process of claim 12 in which tetrahydrofuran is recovered by azeotropic distillation.

17. The process of claim 1 wherein said bottoms fraction has a weight of not greater than 3% of the weight of said feed stream and contains no more than 40% by weight of 1,4-butanediol.

* * * * *

UNITED STATES PATENT AND TRADEMARK OFFICE
CERTIFICATE OF CORRECTION

PATENT NO. : 5,209,825

DATED : May 11, 1993

INVENTOR(S) : Hashim M. Badat, Peter G. Gelblum, Robert E. Trotter

It is certified that error appears in the above-identified patent and that said Letters Patent is hereby corrected as shown below:

Column 7, line 4, change "12" to -- 14 --.

Signed and Sealed this

Fourth Day of January, 1994

*Attest:*

BRUCE LEHMAN

*Attesting Officer*   *Commissioner of Patents and Trademarks*